(12) United States Patent
Kormos et al.

(10) Patent No.: US 6,400,155 B2
(45) Date of Patent: **\*Jun. 4, 2002**

(54) IN-ROOM MRI DISPLAY TERMINAL REMOTE CONTROL SYSTEM

(75) Inventors: Donald W. Kormos, Parma; Mark A. Richard, South Euclid, both of OH (US)

(73) Assignee: Hitachi Medical Corporation (JP)

( \* ) Notice: Subject to any disclaimer, the term of this patent is extended or adjusted under 35 U.S.C. 154(b) by 0 days.

This patent is subject to a terminal disclaimer.

(21) Appl. No.: 09/788,321

(22) Filed: Feb. 16, 2001

Related U.S. Application Data (63) Continuation of application No. 09/200,382, filed on Nov. 24, 1998, now Pat. No. 6,198,285.
(60) Provisional application No. 60/066,981, filed on Nov. 28, 1997.

(51) Int. Cl.$^7$ .................................................. G01V 3/00
(52) U.S. Cl. ....................................... 324/318; 324/322
(58) Field of Search ................................ 324/318, 319, 324/320, 322, 300, 307, 309

(56) References Cited

U.S. PATENT DOCUMENTS 4,347,911 A 9/1982 Bertagna et al. ............ 181/130

(List continued on next page.)

FOREIGN PATENT DOCUMENTS

| DE | 3036217 A1 | 4/1982 |
| DE | 4441169 A1 | 2/1996 |

OTHER PUBLICATIONS

Advertising Literature entitled "*AIRIS*™ *Product Data*" by Hitachi Medical Systems America, Inc., 1995.
Advertising Literature entitled "*AIRIS*™ *Reshaping Open MR*" by Hitachi Medical Systems America, Inc., 1995.
ADS, "In–Room Monitor (MRC)," Jun. 1996.
compu Wiz Productions, "You are now in the presence of the compuWiz, Technolgy At Your Fingertips–RemotePoint PLUS," 1996.
U.S. Department of Health and Human Services, Food and Drug Administration, Center for Devices and Radiological Health, "A Primer on Medical Device Interactions with Magnetic Resonance Imaging Systems," Feb. 7, 1997.
optelecom, "Fiber Optic High Resolution RGB/VGA Video Transmission System with AGC Model 3652T, Model 3652R," May 1996.

*Primary Examiner*—Louis Arana
(74) *Attorney, Agent, or Firm*—Thompson Hine LLP (57) ABSTRACT

An MRI control system for controlling the operation of an MRI scanner from within an RF shielded MRI exam room in which the MRI scanner is located includes an MRI compatible infrared remote control device located within the MRI exam room for producing infrared control signals within the MRI exam room. An infrared receiver is positioned for receiving infrared control signals emitted by the infrared remote control device and producing electrical control signals in response thereto. An MRI controller located outside the MRI exam room is operatively connected to the infrared receiver for receiving control information. The MRI controller is operatively connected to the MRI scanner for controlling the MRI scanner and receiving scan information and the MRI controller operable to control operation of the MRI scanner in response to control signals emitted by the infrared remote control device based upon control information received from the infrared receiver. The system enables a physician or technician to control the operation of the MRI scanner and the images produced from within the MRI exam room as needed, for example, during interventional procedures.

25 Claims, 5 Drawing Sheets

U.S. PATENT DOCUMENTS

| | | | |
|---|---|---|---|
| 4,595,260 A | 6/1986 | Kubota | 350/351 |
| 4,767,969 A | 8/1988 | Green | 315/85 |
| 4,824,210 A | 4/1989 | Shimazaki | 350/331 |
| 4,855,910 A | 8/1989 | Bohning | 364/413 |
| 4,861,142 A | 8/1989 | Tanaka et al. | 350/345 |
| 4,901,141 A | 2/1990 | Costello | 358/93 |
| 4,903,703 A | 2/1990 | Igarashi et al. | 128/653 |
| 4,928,123 A | 5/1990 | Takafuji | 353/20 |
| 4,933,981 A | 6/1990 | Lederer | 381/90 |
| 4,939,464 A | 7/1990 | Hammer | 324/318 |
| 4,981,137 A | 1/1991 | Kondo et al. | 128/653 |
| 4,991,580 A | 2/1991 | Moore | 128/696 |
| 4,991,587 A | 2/1991 | Blakeley et al. | 128/653 |
| 5,022,397 A | 6/1991 | Dumoulin | 128/653 |
| 5,032,689 A | 7/1991 | Halligan et al. | 174/35 |
| 5,076,275 A | 12/1991 | Bechor et al. | 128/653 |
| 5,172,103 A | 12/1992 | Kita | 340/731 |
| 5,184,074 A | 2/1993 | Kaufman et al. | 324/309 |
| 5,365,927 A | 11/1994 | Roemer et al. | 128/653 |
| 5,412,419 A | 5/1995 | Ziarati | 348/61 |
| 5,432,544 A | 7/1995 | Ziarati | 348/61 |
| 5,464,014 A | 11/1995 | Sugahara | 128/653.2 |
| 5,514,833 A | 5/1996 | Kuth | 174/35 |
| 5,638,001 A | 6/1997 | Vrijheid et al. | 324/318 |
| 5,666,055 A | 9/1997 | Jones et al. | 324/318 |
| 5,730,129 A | 3/1998 | Darrow et al. | 128/653 |
| 5,730,134 A | 3/1998 | Dumoulin et al. | 128/653 |
| 5,864,331 A | 1/1999 | Anand et al. | 345/126 |
| 5,978,697 A | 11/1999 | Maytal et al. | 600/411 |
| 6,198,285 B1 * | 3/2001 | Kormos et al. | 324/318 |

* cited by examiner

IN-ROOM MRI DISPLAY TERMINAL REMOTE CONTROL SYSTEM

This Application is a continuation of application Ser. No. 09/200,382 filed Nov. 24, 1998 now U.S. Pat. No. 6,198,215 which claims priority of Provisional Application No. 60/066,981 filed Nov. 28, 1997.

BACKGROUND

The present invention relates to Magnetic Resonance Imaging control systems, and more particularly, to an in-room MRI display terminal and remote control system which enables control of the MRI scanner and the images displayed from within the MRI exam room.

Magnetic Resonance Imaging ("MRI") is a well-known procedure for obtaining detailed, two- and three-dimensional images of a patient based upon nuclear magnetic resonance ("NMR") principles. MRI is well suited for the imaging of soft tissues, and has been used primarily for diagnosing internal injuries or other medical ailments. A typical MRI system will generally include a magnet capable of producing a very strong homogenous magnetic field, sized to cover or surround a portion of a patient's anatomy; a radio frequency ("RF") transmitter and receiver system, including a receiver coil which surrounds the portion of the patient's anatomy under study; a magnetic gradient system to localize in space a particular portion of the patient's anatomy under study; and a computer processing/imaging system for receiving the signals from the receiver coil and for processing the signals into interpretable data, such as visual images for viewing by the physician or MRI attendant. Additional information regarding MRI technology and equipment can be found in Van Nostrand's Scientific Encyclopedia, Eighth Edition, pp. 2198–2201 and U.S. Department of Heath and Human Services, "A Primer on Medical Device Interactions with Magnetic Resonance Imaging Systems," Feb. 7, 1997. The general principles and associated equipment used in MRI is well-known, and as such, additional disclosure is not necessary.

Conventionally, an MRI system will include two rooms: an RF shielded room (Faraday cage) primarily occupied by the MRI magnet and patient table (the "exam room"), and a control room where the other equipment is typically located and where the MRI technologist typically controls the MRI process. The magnet and patient table are located in the shielded exam room. Other equipment is located outside the shielded exam room because, due to the nature of MRI, any device or object transmitting or leaking RF signals can potentially negatively interfere with the imaging process.

The advent of "open" MRI systems provided patients with a more comfortable examination process and also provided the MRI attendants and physicians access to the patient while a portion of that patient is being viewed or scanned by the MRI system. An example of such an open MRI system is the AIRIS® II system, commercially available from Hitachi Medical Systems America, Inc. Open MRI systems enable physicians and other MRI attendants to perform interventional surgery or other therapeutic procedures on the patient while the MRI system is scanning and producing images.

Open MRI systems also facilitate "MR fluoroscopy" which combines near real-time signal acquisition, image reconstitution and image display with such interventional procedures. Accordingly, when utilizing MR fluoroscopy the physician monitors, substantially in real-time (approximately one image per second), a two- or three-dimensional image of the anatomy while performing a medical procedure on that anatomy. For example, if the physician wishes to insert an MR compatible tool, such as a needle or endoscope for example, into a particular organ, while missing other organs, the physician monitors the path of the needle or tool, internally, by viewing the MRI image on a viewing screen. During the MR fluoroscopy procedure, therefore, it is desirable (if not imperative) that a display/control terminal be positioned in close proximity to the physician performing the fluoroscopy procedure; and additionally, it would also be beneficial that this physician be able to easily control the MRI system during the fluoroscopy procedure.

In other intra-operative uses of the MRI machine not necessarily involving the use of MR fluoroscopy, it is often desirable for the image review of just-sequenced patients images to be done inside the MRI exam room since the physician may be unable to leave the MRI exam room due to the desire to maintain as sterile an environment as possible. This problem can arise even in MRI systems in which the scanner is not as "open" as in the AIRIS® II system mentioned above.

A disadvantage with MRI systems is that, due to the high magnetic fields and the susceptibility to RF interference inherent in the MRI process, it is very difficult to locate control/display terminals within the exam room. Video signals transmitted by the remote signal processing systems into the exam room over conductive cables will tend to leak RF interference into the exam room due to the RF frequencies of the video signals. Additionally, in the past the control of the functions and operation of the MRI scanner and displays from within the exam room is limited to function-specific switches (button) and, in the case of graphical user interfaces for in-room control terminals, tethered cursor-control devices (mouse, trackball, joy-stick, etc.) and/or keyboards. Such cursor-control devices require horizontal surface space, which is at a premium in an interventional setting, and tethered devices may severely restrict the physician's location within the exam room.

Accordingly, it would advantageous to allow the physicians or attendants within the exam room to easily view the MRI images and to directly control the MRI system during the fluoroscopy process. It would also be advantageous to provide an MRI system in which images from a number of sources can be displayed selectively under control of the physician or attendant within the exam room. An MRI compatible control system for controlling any piece of equipment from within the MRI exam room would also be advantageous for the medical industry and field.

SUMMARY

In one aspect of the present invention, an MRI control system for controlling the operation of an MRI scanner from within an RF shielded MRI exam room in which the MRI scanner is located includes an MRI compatible infrared remote control device located within the MRI exam room for producing infrared control signals within the MRI exam room. An infrared receiver is positioned for receiving infrared control signals emitted by the infrared remote control device and producing electrical control signals in response thereto. An MRI controller located outside the MRI exam room is operatively connected to the infrared receiver for receiving control information. The MRI controller is operatively connected to the MRI scanner for controlling the MRI scanner and receiving scan information and the MRI controller operable to control operation of the MRI scanner in response to control signals emitted by the infrared remote control device based upon control information received from the infrared receiver. The system enables a physician or technician to control the operation of the MRI scanner and the images produced from within the MRI exam room as needed during interventional procedures.

In a preferred embodiment the display device is an in-room LCD control/display terminal and the infrared remote control is a cordless, hand-held remote for controlling the terminal's operations as well as controlling the examination functions and operation (such as any one or more of start, stop, display images, image review, image selection, enlarge image, reduce image etc.) of the MRI scanner from within the exam room. Preferably, the infrared remote control is adapted for use with MRI applications. In particular, the remote does not emit any significant RF signals, and does not include any significant amounts of ferromagnetic materials. The LCD terminal includes an MRI compatible LCD module mounted within a separate RF shielded space or enclosure, which is also positioned within the exam room. Video signals are transmitted from the MRI controller into the exam room and control signals are transmitted out from the exam room to the computer processors and controls via fiber optic cables. Also, within the separate RF shielded space or enclosure is an IR receiver and the necessary fiber optic transceivers coupled to the LCD display and to the infrared receiver. The fiber optic cables extend from the RF shielded enclosure into the exam room and exit the exam room through a wave guide, which is a shielded connector or other suitable penetration through the exam room shield.

The LCD module preferably displays a graphical user interface which is controlled by the hand-held remote control device. Accordingly, by using the hand-held remote control device, the physician or in-room attendant will be able to initiate sequences, change sequence parameters, photograph, archive, perform post-processing, review images, and transmit images to other areas of the facility via network connections.

In another aspect of the present invention an MRI display system for selectively displaying images within an RF shielded MRI exam room in which an MRI scanner is located includes an MRI compatible infrared remote control device located within the MRI exam room for producing infrared selection signals within the MRI exam room. An infrared receiver is positioned for receiving infrared selection signals emitted by the infrared remote control device and producing electrical control signals in response thereto. A display device is located within the MRI exam room for displaying images. A video switching box is located outside the MRI exam room and has an output operatively connected to the display device within the MRI exam room for providing image signals to the display device. An MR image video signal source located outside or inside the MRI exam room is connected to a first input of the video switching box and a first video device located within the MRI exam room is operatively connected to a second input of the video switching box. The video switching box is controllable by the infrared remote control device for selecting one of the inputs of the video switching box to be displayed by the display device. The system enables video images from multiple sources to be selectively displayed in the MRI exam room, with selection conveniently facilitated from within the MRI exam room.

A further aspect of the present invention provides a control system for controlling one or more devices from within an MRI exam room in which an MRI scanner is located includes an MRI compatible infrared remote control device located within the MRI exam room for producing infrared control signals within the MRI exam room. The infrared remote control device includes substantially no ferromagnetic material such that substantially no attractive force is exerted on the infrared remote control device by large magnetic fields produced within the MRI exam room. An infrared receiver is positioned for receiving infrared control signals emitted by said infrared remote control device and producing electrical control signals in response thereto. The infrared receiver may be connected to any device, within the MRI exam room or outside the MRI exam room, for which control by the infrared remote control device is desired.

DETAILED DESCRIPTION

Figure 1:
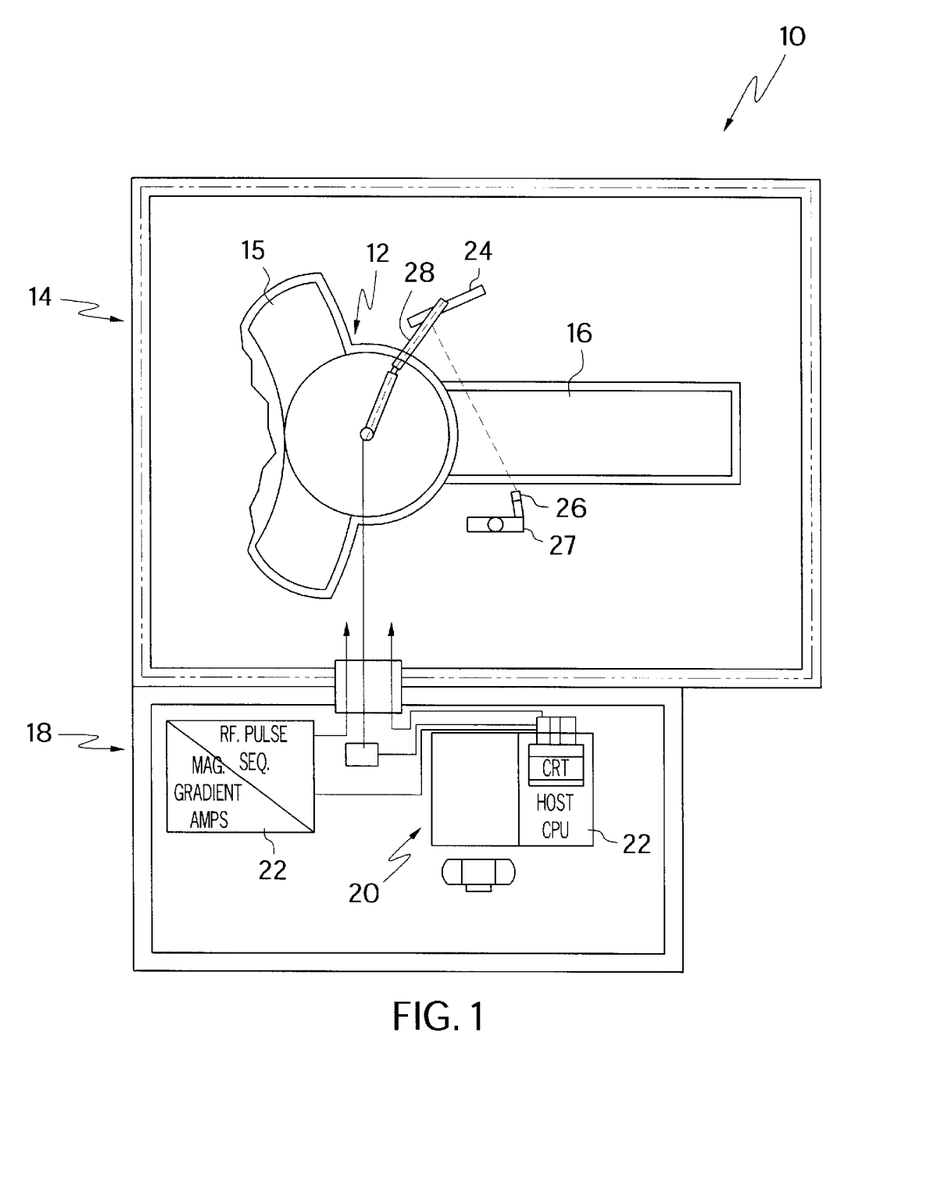

As shown in FIG. 1, a magnetic resonance imaging ("MRI") system 10 includes an MRI scanner 12 located within an RF shielded (Faraday cage) exam room 14. The MRI scanner 12 includes high strength magnets enclosed within a gantry 15 and a motorized patient table 16. A separate room 18 contains the operator's console 20 and the necessary processing/control computer systems, the MRI scanner 12 being connected to MRI controller 22, which term is intended to encompass the assembly of computer and electronic systems utilized to run the MRI scanner and operator's console, or any portion of such assembly, and in the illustrated embodiment includes a host CPU and the electronics (typically an RF pulse sequencer and three magnetic gradient amplifiers for the x, y, and z gradients) for producing the RF pulses and magnetic gradients, to provide scan information to the MRI controller 22 and for receiving scan instructions from the MRI controller 22.

Figure 2:
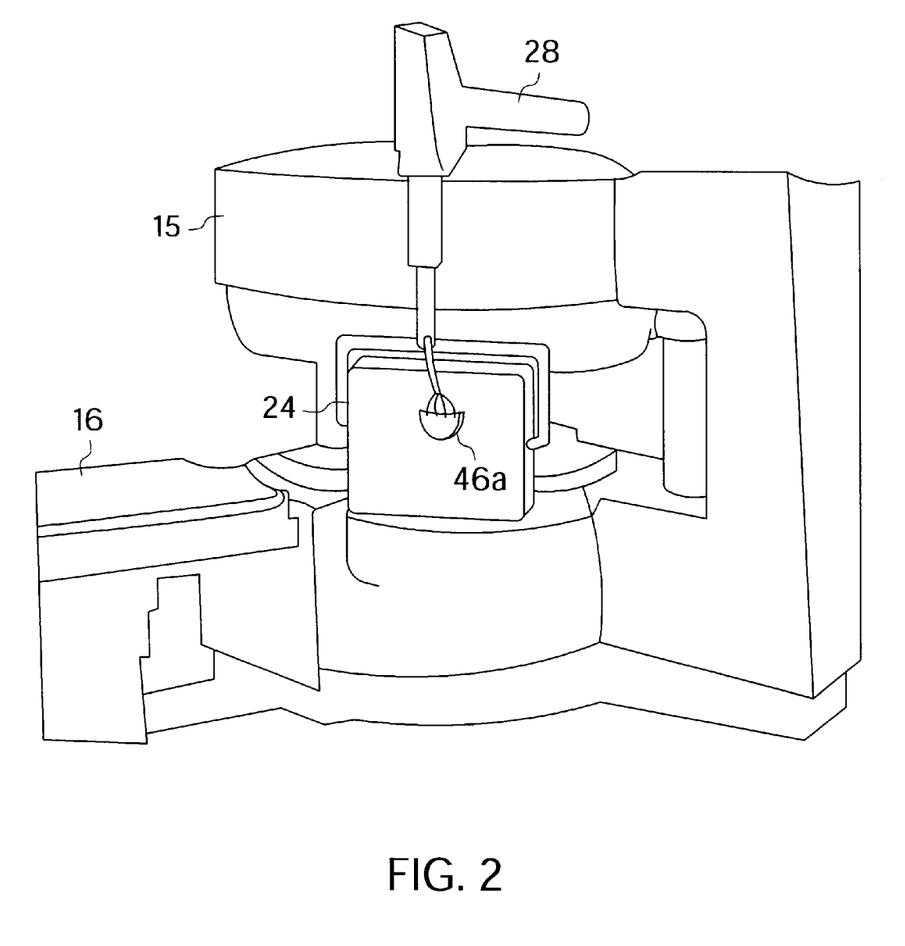
Figure 3:
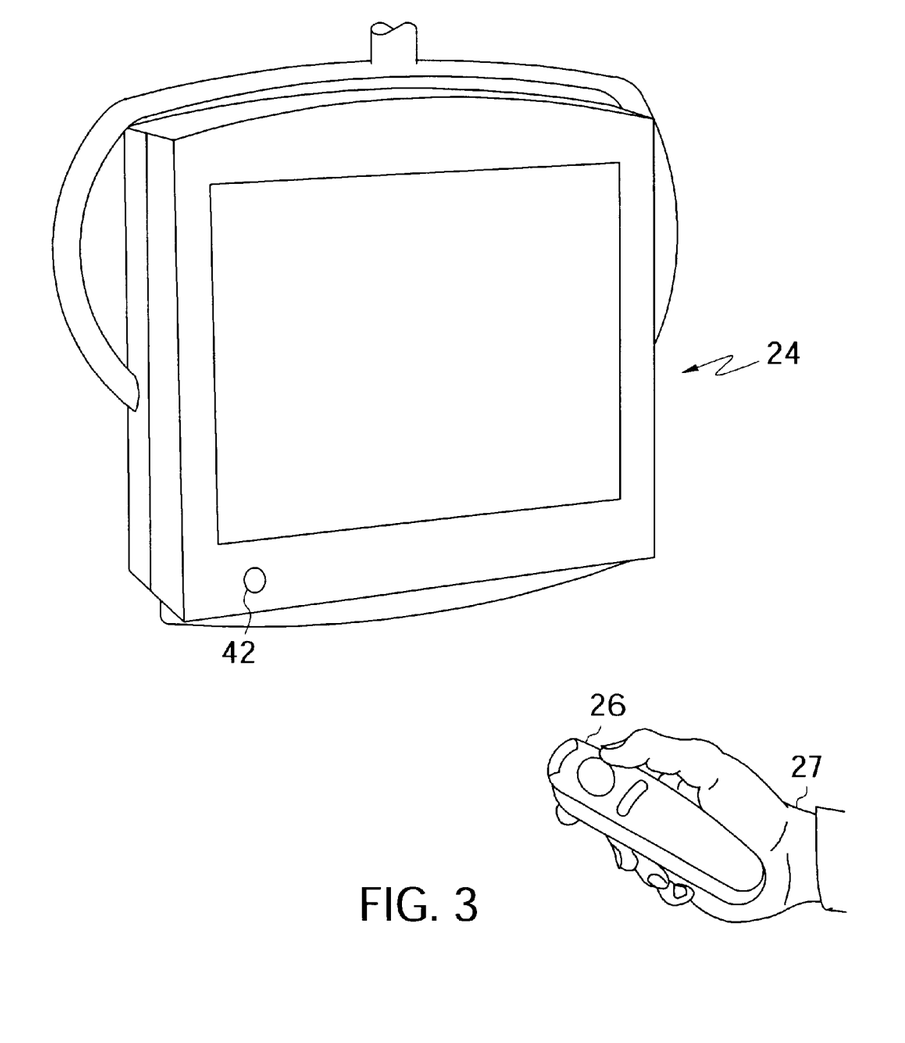

As shown in FIGS. 1–3, in one embodiment the present invention includes an in-room display/control station which includes a display/control terminal 24 and a hand-held remote control device 26, which is operable by the in-room physician or attendant 27. Preferably, the remote control device 26 is an infrared remote control and the display/control terminal 22 is mounted to an arm 28 extending from the gantry 15. However, the display/control terminal 22 could also be separately positioned within the MRI exam room 14, on a separate mount or stand for example.

The remote control device 26 must be MRI compatible, i.e., it must not emit any significant RF signals therefrom and it must not contain any significant amounts of ferromagnetic materials (for the purposes of this disclosure, a "significant" RF signal is any RF signal that will undesirably degrade the performance of the MRI process and a "significant" amount of ferromagnetic material is any amount of ferromagnetic material that will undesirably degrade the performance of the MRI process or will result in a potentially unsafe condition within the exam room—in many cases a "significant" amount will be any amount above zero, however, it is not intended that the present invention be so limited). Generally, if the remote control device 26 contains a sufficiently small amount of ferromagnetic material such that substantially no attractive force is exerted on the device by large magnetic fields within the exam room 14, the remote control device 26 will be suitable for the present invention.

In one embodiment, the remote control device 26 is a RemotePoint or RemotePoint PLUS cordless programmable infrared mouse (commercially available from Interlink Electronics of Camario, Calif.) that has been modified be MR compatible. For example, the three ferromagnetic screws have been replaced with screws of non-ferromagnetic material, the three battery contact terminals have been eliminated, and the batteries have been replaced with a lithium cell battery such as an Ultralife U3VL-NM-TS battery with a plastic case and stainless steel components. Due to the size of the MR compatible battery, the battery compartment was also redesigned as necessary. The remote control device 26 of the present invention has the advantage in that it can be used safely within the exam room 14 and that it can transmit the infrared signal through the magnetic field to the display/control terminal 24 without degrading the performance of the MRI system.

Figure 4:
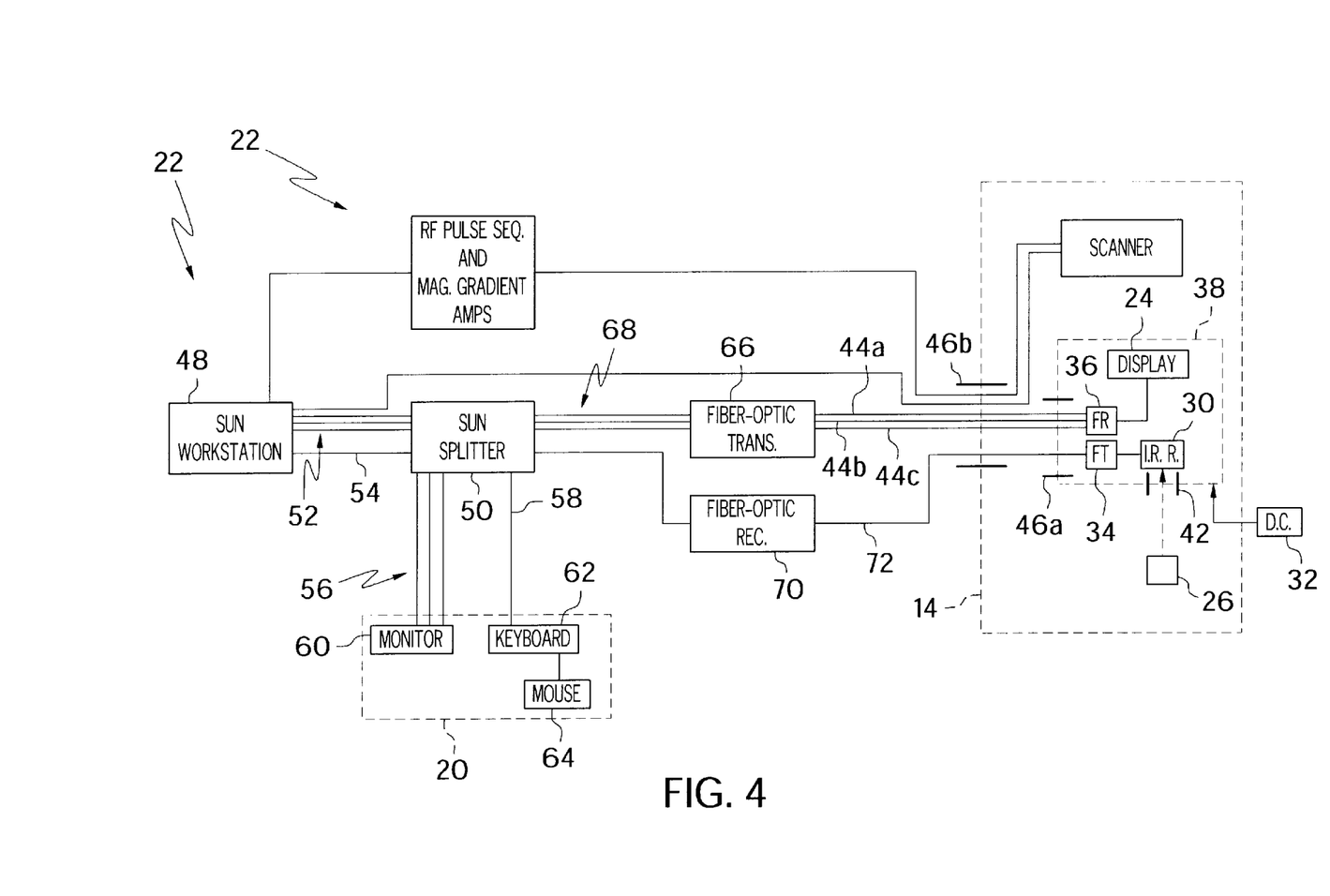

The display/control terminal 24, modified to be MR compatible, includes an internal LCD module, containing a liquid crystal "glass," fluorescent back lighting and associated interface circuitry. Power is transmitted to the module from a remote power source 32. As shown in FIG. 4, the display/control terminal 24 also includes an infrared receiver 30, a fiber optic transmitter 34 and a fiber optic receiver 36. All of these components are housed within a further RF shielded (Faraday cage) casing or space 38 within the MRI exam room 14. Although RF shielded space 38 is shown as one shielded space enclosing display 24, infrared receiver 30, fiber optic transmitter 34, and fiber optic receiver 36, it is recognized that the use of multiple, separate RF shielded spaces containing individual components is possible. Accordingly, as used herein the terminology further RF shielded space is intended to encompass the use of one or more separate RF shielded spaces to enclose any of components 24, 30, 34 and 36. The casing defining further RF shielded space 38 includes a lining of appropriate RF shielding material such as a stainless steel mesh coated with silver, blackened and placed in plastic as available from DONTECH of Doylestown, Pa. Other RF shielding materials might also be used. The casing is coupled to the arm 28 by a cast aluminum support structure 40. The casing also includes a small port 42 optically coupled to the infrared receiver 30 for receiving infrared signals from the remote control device 26. The infrared receiver 30 is operatively coupled to the fiber optic transmitter 34 so that the physician or in-room attendant can transmit control information, using the remote control device 26, out to the MRI controller 22. As will be described below, these control signals are transmitted out of the exam room 14 over a discrete fiber optic cable 72. Coupled to the fiber optic receiver 36 are three fiber optic video input lines 44a, 44b and 44c, corresponding to the three video lines of a conventional RGB cable. Wave guide 46a is provided for the entry of fiber optic video lines 44a–44c, as well as the fiber optic line 72, into the shielded space 38 and wave guide 46b is provided for the entry of the fiber optic lines through the exam room RF boundary or shield 14. Fiber optic receiver 36 may be a standard fiber optic video receiver adapted for use in MRI exam room 14. For example, where the fiber optic receiver 36 includes one or more iron core transformers, such as a DC to DC transformer to provide a negative synch voltage, the iron core transformers are preferably removed and replaced with air core transformers or a separate input line to space 38 may be necessary to provide the DC voltage. It is likewise recognized that other components may need to be similarly modified.

The LCD module portion of the display/control terminal 24 is preferably a modified LCD 2000 monitor, commercially available from NEC Technology. To modify the LCD 2000 monitor for use as the LCD module for the present invention, the plastic casing of the LCD 2000 monitor is removed and replaced with an RF shielding housing or casing such as described above, the power supply is removed (the power supply includes large iron-core transformers there within) and replaced with a shielded wire coupled to the remote power source 32, the transformers in the fluorescent back-light power supply are replaced with air-core transformers, any other ferromagnetic components are replaced with non-ferromagnetic components, and the fiber optic receiver interface 36 is incorporated into the RGB receiver. It should be apparent to those of ordinary skill that the display/control terminal 24 (not emitting significant RF signals, including fiber optic transmitters and receivers, including an infrared receiver for remote operation, and housed within a shielded casing) will have many alternate uses outside of the MRI technology. Such a display/control terminal will have use in various environments where radio interference may pose a problem. Additionally, the fiber optic lines allow for the transmission of the video and control signals over very long distances without significant degradation of the data.

As is further shown in FIG. 4, the control room 18 preferably includes a Sun Microsystems workstation 48; a Network Technologies Vopex 2K-Sun peripheral splitter 50, operatively coupled to the workstation 48 by an RGB cable 52 and a keyboard cable 54; an operator's console 20 operatively coupled to the peripheral splitter 50 by an RGB cable 56 and a keyboard cable 58, where the operator's console includes a monitor 60, a keyboard 62 and a cursor control device such as a mouse 64; a fiber optic transmitter 66 (such as model 3652T available from Optelcom of Gaithersburg, Md.) for converting the video signals on an RGB cable 68, extending from the peripheral splitter 50, into fiber optic signals transmitted over the fiber optic lines 44a–44c into the exam room 14; and a fiber optic receiver 70 (such as model 3652R available from Optelcom of Gaithersburg, Md.) for receiving control signals over a fiber optic line 72 which is coupled to the fiber optic transmitter 34. The fiber optic receiver 70 converts the fiber optic signals into electrical signals which are transferred back to the workstation 48 through splitter 50. As noted above any such components placed within the MRI exam room 14 may require modifications for MRI compatibility such as removing ferromagnetic materials and replacing them with non-ferromagnetic materials and removing iron core transformers and replacing them or providing a separate input line to provide DC voltages.

Accordingly, the physician or attendant within the exam room 14 can control the operation of the MRI device as well as the operation of the display/control terminal 24 by using the hand-held remote 26. The IR receiver 30 receives control signals from the IR remote 26, and the control signals are converted into fiber optic signals by the fiber optic transmitter 34 which are then sent over the fiber optic line 72 to the fiber optic receiver 70 in the operator station. The workstation 48 processes these control signals, generates display signals, and then transmits these display signals over the RGB cables 52, 68, to the fiber optic transmitter 66, which converts these display signals into fiber optic signals and transmits them into the exam room 14 over fiber optic lines 44a–44c. These fiber optic signals are received by the fiber optic receiver 36 and the internal video circuitry processes these signals received on the fiber optic receiver into a video display which is displayed on the display 24. The remote control system can be utilized to control the functions and operation of the MRI scanner using a graphical user interface in much the same manner as a technician within the control room 18 might using the operator's console 20 including mouse 64 and monitor 60, except that the present invention facilitates such control from within the exam room 14.

It will be apparent to one of ordinary skill in the art that in another aspect of the invention, fiber optic interfaces may be included for other MR compatible video devices (other than the display terminal) and other MR compatible equipment used within the examination suite. Additionally, it is within the scope of the invention to utilize fiber optics to convey video signals sourced inside the MR examination suite, out of the RF shielded exam room 14 using an RF shielded fiber optic transmitter located within the suite. It is also within the scope of the invention to utilize a display module utilizing display technologies other than LCD display technology. For example, it is within the scope of the invention that the display/control terminal utilizes field emission display ("FED") technology (such as available from PixTech of Santa Clara, Calif.) or plasma display technology (such as available from NEC Technology). The use of the fiber optic technology with the present invention provides for the safe and RF free transmission of video and other signals to and from the exam room. Once inside the exam room, the fiber optic signals are reconverted, preferably within a separately shielded casing or space, into electric signals that are used by a component within the exam room. RF wave guides are preferably employed as a means to pass the fiber optic cables through the RF shielded room and into the RF shielded equipment within the room.

It is also within the scope of the invention that remote control devices, other than the hand-held remote 26, are utilized, such as infrared computer keyboards, cordless infrared track ball devices, infrared cordless switches, and the like. Of course, all of these alternate control devices must be MR compatible as described above. Such remote control devices may have function specific buttons thereon for activating/deactivating individual processes or actions of the MRI system, such as "start,""stop"or "scan"or may be utilized in connection with a graphical user interface.

Furthermore, although the preferred embodiment locates the infrared receiver 30 within the shielded casing or space 38 with the display terminal 24, it is within the scope of the present invention to provide a separately shielded housing for the infrared receiver 30 and associated fiber optic transmitter 34 as previously mentioned. Also, it is within the scope of the invention that an infrared receiver be located outside of the examination suite, which would receive IR signals from the hand-held remote through a wire mesh RF window. Furthermore, it is within the scope of the invention that the hand-held remote be used to control other devices and machines within the examination suite. These devices include patient monitoring devices, audio video equipment, computer work stations, etc.

Figure 5:
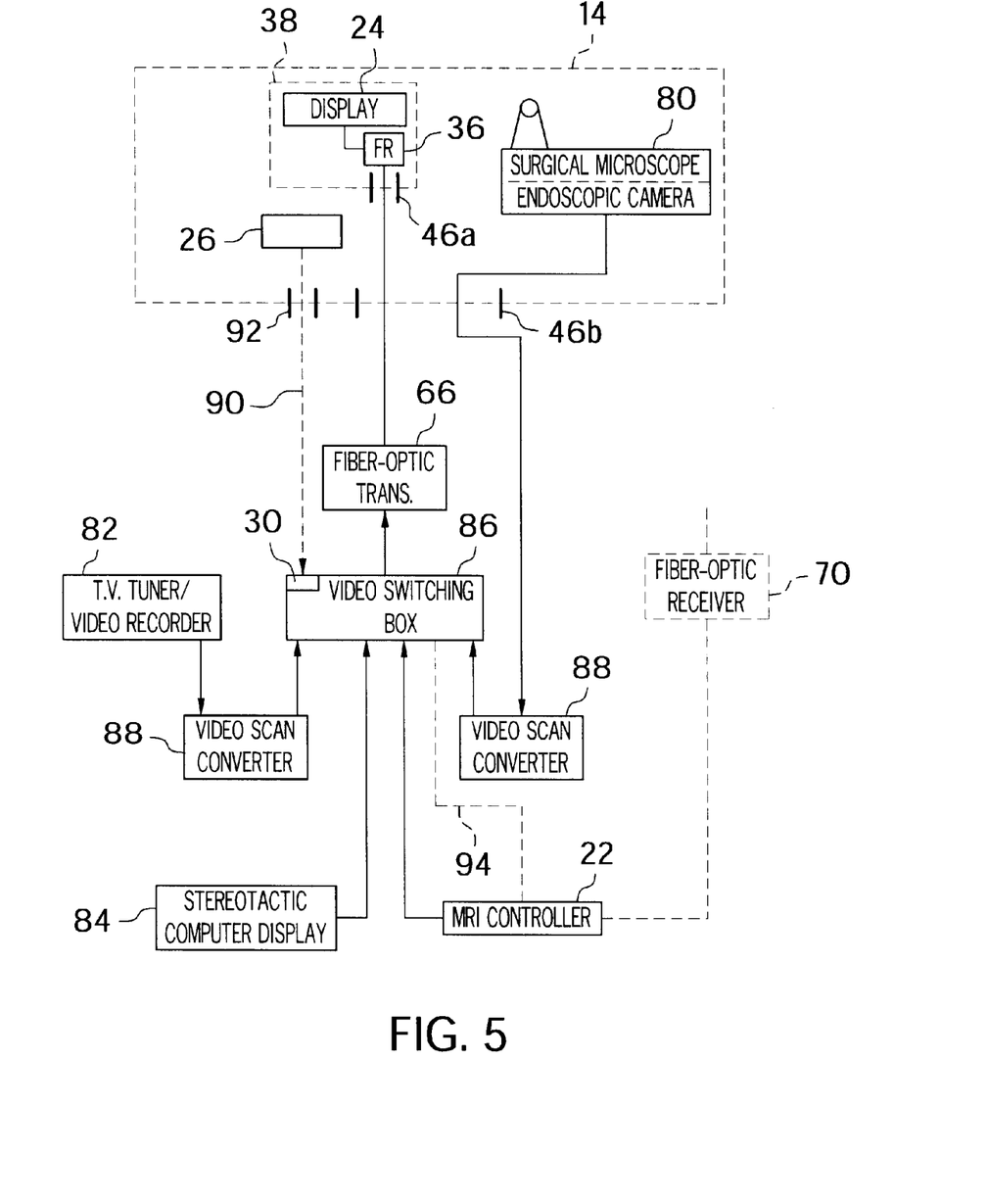

Accordingly, another aspect of the invention incorporating various of the above modifications is depicted in FIG. 5 for selectively displaying images from multiple video devices or sources. The video sources include MRI scan images from MRI controller 22 (shown in simplified form), an in-room video device 80 such as a surgical microscope or endoscopic camera, a T.V. tuner or video recorder 82, or a stereotactic computer display 84. Other known video devices may also be incorporated into such a system. The output of each video device is connected to an input of video switching box 86 (such as model SE-SC4-IR available from Network Technologies of Aurora, Ohio) which in turn is connected to fiber optic transmitter 66 which in turn is connected to fiber optic receiver 36 as previously described. Video scan converters may be utilized as necessary between the video devices and the video switching box 86. Video switching box 86 includes an associated infrared receiver 30 for receiving infrared control signals from infrared remote control device 26 within exam room 14. In this regard, an infrared path 90 is provided through a wire mesh RF window 92 to video switching box 86 such that the box is responsive to infrared control signals. As shown video switching box 86 is a four input-one output device with the output being selectable by infrared remote control device 26. The connection between video devices 80 within exam room 14 and the video switching box 86 could include fiber optic links as previously described. It is recognized that such video selection could also be incorporated into a system such as that of FIG. 4 where the infrared receiver 30 is located within further RF shielded space 38 in which case the infrared receiver 30 would be connected to a fiber optic transmitter which in turn connects to fiber optic receiver 70 (shown in dashed lines) with the fiber optic receiver 70 connected to the MRI controller 22. The MRI controller 22 could then include a selection output connected to a control input of video switching box 86 as indicated by dashed line 94, with the MRI controller programmed to act as a switch controller in response to infrared control signals. Likewise, a separate switch controller could be utilized or the switch controller might be in incorporated into the video switching box 86.

While the forms of apparatus herein described constitute preferred embodiments of this invention, it is to be understood that the invention is not limited to these precise forms of apparatus, and that changes may be made therein without departing from the scope of the invention. In this regard, although use of an infrared remote control device is preferred it is recognized that in some applications a properly filtered RF remote control might be used where the RF control signal produced is established outside a range which might effect the MRI scanner. For example, for the AIRIS® II system operating at 12.7 MHZ RF remote control signals below about 12.3 MHZ or above about 13.1 MHZ would have little or no effect on operation of the MRI scanner. Further, although an operator's console 20 is shown in separate room 18, it is recognized that with the in-room control system of the present invention the operator's console could be eliminated if necessary or desirable, and the separate control room 18 could effectively be reduced to a control closet for housing the controller 22.

What is claimed is:

1. An MRI control system for controlling the operation of an MRI scanner from within an MRI exam room in which the MRI scanner is located, an RF shield defining a boundary of the MRI exam room, said control system comprising:

an MRI compatible infrared remote control device located within the MRI exam room for producing infrared control signals within the MRI exam room, said infrared remote control device adapted for use by a doctor or technician within the MRI exam room;

an infrared receiver positioned for receiving infrared control signals emitted by said infrared remote control device and producing electrical control signals in response thereto;

an MRI controller located outside the boundary of the MRI exam room, said MRI controller operatively connected to said infrared receiver for receiving control information, said MRI controller operatively connected to the MRI scanner for controlling the MRI scanner and receiving scan information, said MRI controller operable to control operation of the MRI scanner in response to infrared control signals emitted by said infrared remote control device based upon control information received from said infrared receiver.

2. The MRI control system of claim 1 further comprising a further RF shielded space located within the MRI exam room, wherein said infrared receiver is positioned within said further RF shielded space of the MRI exam room.

3. The MRI control system of claim 2, further comprising a first fiber optic transmitter located within said further RF shielded space of the MRI exam room and at least one fiber optic cable connected to said first fiber optic transmitter and extending from said further RF shielded space of the MRI exam room, through the boundary of the MRI exam room to a first fiber optic receiver connected to said MRI controller, said infrared receiver operatively connected to said first fiber optic transmitter for providing signals to said first fiber optic transmitter.

4. The MRI control system of claim 3 further comprising a first waveguide positioned between said further RF shielded space and the MRI exam room and a second waveguide positioned between the MRI exam room and said controller, wherein said at least one fiber optic cable extends through each of said first and second waveguides.

5. The MRI control system of claim 3 further comprising a display device located within said further RF shielded space of the MRI exam room.

6. The MRI control system of claim 5 further comprising a second fiber optic transmitter located outside the MRI exam room and operatively connected to said MRI controller for receiving MR image signals therefrom, a second fiber optic receiver located within said further RF shielded space of the MRI exam room, and at least one fiber optic video line connected between said second fiber optic transmitter and said second fiber optic receiver, said display device operatively connected to said second fiber optic receiver for display of MR images.

7. The MRI control system of claim 6 wherein said MRI controller is operable to produce signals which effect display of MRI scanner control graphics on said display device, and wherein said infrared remote control device enables control of the MRI scanner via selection and adjustment of said displayed MRI control graphics.

8. The MRI control system of claim 6 further comprising a video switching box located outside the boundary of the MRI exam room and connected to an input of said second fiber optic transmitter, a first video device located within the MRI exam room and operatively connected to a first video input of said video switching box, wherein said MRI controller is connected to said second fiber optic transmitter through a second video input of said video switching box, and wherein said video switching box is controllable by said infrared remote control device.

9. The MRI control system of claim 8 wherein said MRI controller includes a video selection output connected to said video switching box for selecting the video input provided to said second fiber optic transmitter, said MRI controller operable to establish such selection based upon received control information.

10. The MRI control system of claim 5 wherein said further RF shielded space is defined by a housing of said display device.

11. The MRI control system of claim 1 wherein said infrared remote control device includes substantially no ferromagnetic material such that substantially no attractive force is exerted on said infrared remote control device by large magnetic fields produced within the MRI exam room.

12. The MRI control system of claim 1 wherein said infrared receiver is located outside the boundary of the MRI exam room, and wherein said MRI control system further comprises an RF shielded infrared signal path extending through a boundary of the MRI exam room, said infrared receiver positioned relative to said path so as to receive infrared signals generated within the MRI exam room and along said path.

13. The MRI control system of claim 1 wherein said infrared remote control device comprises a hand-held remote control device.

14. The MRI control system of claim 1 wherein said MRI controller is located within a control closet.

15. An MRI display system for selectively displaying images within an MRI exam room in which an MRI scanner is located, an RF shield defining a boundary of the MRI exam room, said display system comprising:

an MRI compatible infrared remote control device located within the MRI exam room for producing infrared selection signals within the MRI exam room, said infrared remote control device adapted for use by a doctor or technician within the MRI exam room;

an infrared receiver positioned for receiving infrared selection signals emitted by said infrared remote control device and producing electrical control signals in response thereto;

a display device located within the MRI exam room for displaying images;

a video switching box located outside the boundary of the MRI exam room and having an output operatively connected to said display device within the MRI exam room for providing image signals thereto;

an MR image video signal source located outside the boundary of the MRI exam room and connected to a first input of said video switching box;

a first video device located within the MRI exam room and operatively connected to a second input of said video switching box; and wherein said video switching box is controllable by said infrared remote control device for selecting one of the inputs of said video switching box to be displayed by said display device.

16. The MRI control system of claim 15 further comprising at least one other video source connected to a third input of said video switching box.

17. The MRI control system of claim 15 wherein said display device comprises an LCD display monitor.

18. An MRI control system for controlling the operation of an MRI scanner from within an MRI exam room in which the MRI scanner is located, an RF shield defining a boundary of the MRI exam room, said control system comprising:

an MRI compatible remote control device located within the MRI exam room for producing control signals within the MRI exam room, said remote control device adapted for use by a doctor or technician within the MRI exam room;

a receiver positioned for receiving control signals emitted by said remote control device and producing electrical control signals in response thereto;

an MRI controller located outside the boundary of the MRI exam room, said MRI controller operatively connected to said receiver for receiving control information, said MRI controller operatively connected to the MRI scanner for controlling the MRI scanner and receiving scan information, said MRI controller operable to control operation of the MRI scanner in response to control signals emitted by said remote control device based upon control information received from said receiver.

19. The MRI control system of claim 18 wherein said remote control device comprises an RF remote control device producing control signals at a frequency outside a range which affects operation of the MRI scanner.

20. The MRI control system of claim 19 further comprising a display device located within said further RF shielded space of the MRI exam room.

21. The MRI control system of claim 18 further comprising a further RF shielded space located within the MRI exam room, wherein said infrared receiver is positioned within said further RF shielded space of the MRI exam room.

22. A combination display and control apparatus installable in an MRI exam room for use in connection with an MRI scanner and an MRI controller, the display apparatus comprising:

a display terminal for displaying images;

an RF shielded space defined at least in part by an RF shielded casing which extends from the display terminal;

an infrared receiver positioned within the RF shielded space for receiving infrared control signals;

a fiber optic transmitter located within said RF shielded space, said infrared receiver operatively connected to said fiber optic transmitter for providing signals to said fiber optic transmitter; and a fiber optic receiver located within said RF shielded space for receiving fiber optic display control signals, the fiber optic receiver operatively connected to the display terminal for controlling images displayed by the display terminal.

23. The apparatus of claim 22 further comprising:

a waveguide through said RF shielded casing for permitting fiber optic cables to pass from an exterior of the RF shielded casing to the fiber optic transmitter and the fiber optic receiver within the RF shielded space.

24. The apparatus of claim 23 wherein the RF shielded casing includes a port for permitting entry of infrared control signals.

25. The apparatus of claim 24 wherein the RF shielded casing includes a stainless steel mesh type RF shielding material.

* * * * *

UNITED STATES PATENT AND TRADEMARK OFFICE
CERTIFICATE OF CORRECTION

PATENT NO.     : 6,400,155 B2
DATED          : June 4, 2002
INVENTOR(S)    : Donald W. Kormos et al.

It is certified that error appears in the above-identified patent and that said Letters Patent is hereby corrected as shown below:

Title page,
Title, insert -- AND -- after the word "TERMINAL"

Column 11,
Line 5, after the word claim "19" should be -- 21 --
Line 10, after the word "said" delete the word "infrared"

Signed and Sealed this

Twelfth Day of November, 2002

Attest:

Attesting Officer

JAMES E. ROGAN
Director of the United States Patent and Trademark Office